(12) United States Patent
Bouvier et al.

(10) Patent No.: US 11,191,866 B2
(45) Date of Patent: Dec. 7, 2021

(54) DRESSING ENABLING THE CONTROLLED AND PROLONGED RELEASE OF METFORMIN

(71) Applicant: Urgo Recherche Innovation et Developpement, Chenove (FR)

(72) Inventors: Claire Bouvier, Dijon (FR); Nathalie Derain, Prenois (FR); Sebastien Very, Epernay sous Gevrey (FR); Aline Grandjean, Rouvres-en-Plaine (FR)

(73) Assignee: Urgo Recherche Innovation et Developpement, Chenove (FR)

( * ) Notice: Subject to any disclaimer, the term of this patent is extended or adjusted under 35 U.S.C. 154(b) by 0 days.

(21) Appl. No.: 16/317,120

(22) PCT Filed: Jul. 12, 2017

(86) PCT No.: PCT/FR2017/051910
§ 371 (c)(1),
(2) Date: Jan. 11, 2019

(87) PCT Pub. No.: WO2018/011520
PCT Pub. Date: Jan. 18, 2018

(65) Prior Publication Data
US 2019/0184055 A1 Jun. 20, 2019

(30) Foreign Application Priority Data
Jul. 12, 2016 (FR) ...................................... 1656677

(51) Int. Cl.
| | | |
|---|---|---|
| *A61K 31/155* | (2006.01) |
| *A61L 15/24* | (2006.01) |
| *A61L 15/34* | (2006.01) |
| *A61L 15/44* | (2006.01) |
| *C08L 9/00* | (2006.01) |
| *C08L 53/02* | (2006.01) |
| *C08L 91/08* | (2006.01) |
| *C08L 1/28* | (2006.01) |
| *C08L 91/00* | (2006.01) |

(52) U.S. Cl.
CPC ............ *A61L 15/44* (2013.01); *A61K 31/155* (2013.01); *A61L 15/24* (2013.01); *A61L 15/34* (2013.01); *C08L 1/286* (2013.01); *C08L 9/00* (2013.01); *C08L 53/025* (2013.01); *C08L 91/00* (2013.01); *C08L 91/08* (2013.01); *A61L 2300/206* (2013.01); *A61L 2300/40* (2013.01); *C08L 2203/02* (2013.01); *C08L 2205/02* (2013.01)

(58) Field of Classification Search
None
See application file for complete search history.

(56) References Cited

U.S. PATENT DOCUMENTS

2014/0142526 A1* 5/2014 Auguste ................ A61F 13/023
604/365

FOREIGN PATENT DOCUMENTS

| CN | 105125539 | * 12/2015 | ........... A61K 31/155 |
| WO | 2016/097653 A1 | 6/2016 | |

OTHER PUBLICATIONS

International Search Report issued in corresponding International Patent Application No. PCT/FR2017/051910 dated Oct. 13, 2017.

* cited by examiner

*Primary Examiner* — Brian Gulledge
(74) *Attorney, Agent, or Firm* — Morgan, Lewis & Bockius LLP (57) ABSTRACT

The subject matter of the present invention is, according to a first aspect, a dressing comprising an interface layer, characterised in that said interface layer comprises a weave coated with an elastomeric matrix comprising metformin, the salts and the complexes thereof. The subject matter of the invention is also a dressing comprising metformin, characterised in that the percentage of metformin released after 72 hours is between 40 and 100% of the quantity of metformin inserted in the dressing. Moreover, the subject matter of the invention is a method for producing said dressing as well as the use thereof for healing a wound.

12 Claims, 6 Drawing Sheets

DRESSING ENABLING THE CONTROLLED AND PROLONGED RELEASE OF METFORMIN

SUMMARY

The present invention relates to a dressing that allows for the controlled and prolonged release of metformin.

PRIOR ART

The healing of wounds generally depends on the proliferation of new epithelial, endothelial and connective tissues. It therefore calls into play a set of events that are nested and interconnected by successive and reciprocal inductions of the various cells involved. Each step is induced by the previous step and therefore can unfold only if the previous step has terminated. This is a complex process subtended by successive waves of growth factors and inflammatory mediators.

The pharmaceutical market currently offers many topical preparations recommended for favouring the healing of. In fact, their action results from the complementarity of the various products that they are comprised of and provide them, up to a certain limit, with their healing property. They protect the wounds from the surrounding environment via an antiseptic coating. They stimulate the development of the vascularisation and regulate epidermalisation. These topical forms are primarily comprised of a lipid mixture (lanolin, vaseline, glycerine . . . ) to which are added acids (salicylic, benzoic, malic), minerals (zinc oxide, titanium oxide) or halides (starch iodide). Some also contain collagen, fibrinogen, serum enzymatic proteolysis (supply of amino acids) or vitamins (vitamin A) of hormones (chloro-4 testosterone acetate). There is also an ointment (Madecassol tulgras from Laboratoires SYNTEX) of which the healing action is supplied by the combination of a mixture of three triterpenes extracted from roots of the Centella asiatica plant (TCEA). These compounds stimulate the biosynthesis of collagen and of glycoaminoglycans. Patent FR 2 809 310 describes the use of metformin in a topical composition that has a healing and/or angiogenic effect. The various galenic forms of compositions considered are of the oil, cream, foam, liniment, lotion, ointment, liquid, gel, milk, powder or spray type.

However, the local application of metformin in the form of a topical composition requires being frequently repeated in order to ensure an effect on the healing. Studies on rats have in particular shown that the metformin that is radioactively marked and deposited on a wound in a gel remained for a very short period of time at the local level. Indeed, metformin is an extremely hydrophilic compound, which makes it easily soluble in the exsudates and leads to a very rapid passage of it on the wound. The contact time between metformin and the receptors of the wound that require being activated locally is therefore very short and which leads to a low pharmacological response.

Furthermore, the topical compositions of the type of those proposed in patent FR 2 809 310 do not make it possible to treat the wound for more than a few hours. It is required to regularly refresh the application thereof. Yet, for many wounds, it is necessary to apply a local treatment that favours healing for several days, even several weeks, in order to obtain good healing, and to prevent the refreshing of the treatment in order to limit the risks of infection linked to the handling of the compositions.

It would therefore be desirable to have a device, such as a dressing, comprising metformin, to effectively treat the wounds for several days. For economic reasons, the dressing should ideally be applied for a duration of approximately 72 h. Changing a dressing too frequently induces additional costs with regards to the costs of the caregivers required to change said dressing. Excessively frequent changing can also increase the risk of infections. Indeed, when the dressing is removed, the wound is exposed to the bacteria present in the environment.

However, in light of the strong affinity of metformin for exsudates, the latter tends to be released too quickly on the wound, in such a way that a peak in the concentration of metformin is released by the dressing within the hours after it has been applied, and the beneficial effects of the treatment thus do not last for more than a few hours. The dressing should on the contrary allow for a controlled and continuous release of the metformin for several days, in particular for approximately three days. In particular, in order to achieve a satisfactory response level on receptors of the wound, a sufficient quantity of metformin should be released as soon as the device is applied, then a slower but continuous release of metformin should be maintained throughout the entire duration of application of the device on the wound in order to maintain the desired effects. This entails, in other terms, administering a particular release profile that involves a bolus in the first times of application of the formulation, then the maintaining of a lower level of release of metformin throughout the entire duration of the treatment.

SUMMARY OF THE INVENTION

The present invention aims to respond to these problems, by proposing a device of the dressing type comprising metformin, allowing for a releasing of the latter according to a continuous and controlled profile for several days.

The invention thus has as subject matter, according to a first aspect, a dressing comprising an interface layer comprising an elastomeric matrix, said matrix comprising metformin, the salts and the complexes thereof, characterised in that the metformin has a particle size defined by a d50<300 µm and a d90<600 µm. The dressing according to the invention can have the form of a weave coated with such an elastomeric matrix, or of a self-supported interface dressing comprising said non-supported elastomeric matrix.

The subject matter of the invention is also a dressing comprising metformin, characterised in that the percentage of metformin released after 72 hours is between 40 and 100% of the quantity of metformin inserted in the dressing.

Moreover, the subject matter of the invention is a method for producing a dressing such as described hereinabove, characterised in that it comprises:

1. the preparing of an interface layer formed from an elastomeric matrix by:
    i. preparing an elastomeric matrix by dispersion of the metformin having a particle size defined by a d50<300 µm and a d90<600 µm, the salts and the complexes thereof in an elastomer,
    ii. the coating of a weave with the elastomeric matrix prepared in the step i or the hot casting of said matrix, preferably on an engraved plate forming for example the imprint of a net or grid with a square mesh
2. optionally the covering of the interface layer with at least one absorbent layer
3. optionally the maintaining of the interface layer and of the possible absorbent layer by a strip or an adhesive support intended to be fastened onto the peripheral zones of healthy skin far from the wound.

According to another embodiment, the subject matter of the invention is a dressing, for the use thereof for healing a wound or the use of such a dressing for healing a wound.

DETAILED DESCRIPTION

Interface Layer

The dressing according to the present invention comprises an interface layer comprising an elastomeric matrix, said elastomeric matrix comprising metformin having a particle size defined by a d50<300 μm and a d90<600 μm, the salts and the complexes thereof. The interface layer of the dressing is in particular intended to be placed in contact with the wound.

The elastomeric matrix in particular comprises at least one elastomer.

Elastomer

Preferably, the elastomer can be chosen from triblock sequenced polymers of the ABA type comprising two terminal A styrene blocks and a central sequence B which is a saturated olefin such as for example ethylene-butylene or ethylene-propylene. These triblock copolymers may optionally be combined with diblock copolymers of the AB type comprising an A styrene block and a B ethylene-propylene or ethylene-butylene block. In the case of a mixture of ABA triblock copolymers and of AB diblock copolymers, already available commercial mixtures of ABA triblock copolymers and of AB diblock copolymers can be used or made from mixtures of any proportion chosen beforehand from two products that are independently available. Such triblock copolymers with a saturated central sequence are well known to those skilled in the art and are for example marketed:

by the company KRATON POLYMERS under the name KRATON G®, and in particular under the name KRATON G1651®, KRATON G1654® or KRATON G1652® for the poly(styrene-(-ethylene-butylene-)-styrene) sequenced copolymers (with SEBS abstract);

by the company KURARAY under the name SEPTON® for the poly(styrene-(-ethylene-propylene-)-styrene) sequenced copolymers (with SEPS abstract).

As an example of commercial mixtures of triblock and diblock copolymers, mention can be made of the product marketed by the company KRATON POLYMERS under the name KRATON G1657® of which the olefin sequence is ethylene-butylene.

As an example of a particular mixture of triblock and diblock copolymers that can be produced in the framework of the present invention, mention can be made of the mixture:

of a triblock SEBS, such as in particular the product marketed by the company KRATON POLYMERS under the name KRATON G16510; and of a poly(styrene-olefin) diblock copolymer such as in particular poly(styrene-ethylene-propylene) marketed by the company KRATON POLYMERS under the name KRATON G1702®.

In the framework of the present invention, the SEBS or SEPS triblock copolymers are preferred that have a styrene content between 25 and 45% by weight in relation to the weight of said SEBS or SEPS and having an average or high molecular weight and a Brookfield viscosity at least equal to 300 cPs (measurement taken at 25° C. for a solution at 10% in the toluene).

Even more preferably, triblock sequences copolymers alone will be used, preferably SEBS triblock copolymers and in particular the products marketed by the company KRATON POLYMERS under the names KRATON G1650®, KRATON G1651® or KRATON G1654®. KRATON G1651® has chain lengths that are longer than those present on Kraton G1654®. Thus, KRATON G1651® has a molecular weight of 213,000-240,000 Da and KRATON G 1654 has a molecular weight of 180,000 Da. This difference in molecular weight is able to impact the Brookfield viscosity at 25° C. for a solution at 10% of elastomer. Thus, the Brookfield viscosity at 25° C. for a solution at 10% of KRATON G1651® is 1,800 cPs compared to 410 cPs for KRATON G1654®. Likewise the melt flow under a stress of 5 kg is also affected by this variation in molecular weight: it is 5 g/10 min for KRATON G1651® compared to 22 g/10 min for KRATON G1654®.

Preferably, the elastomer can be chosen from the poly (styrene-(-ethylene-butylene-)-styrene) sequenced copolymers with a high molecular weight, i.e. having a molecular weight greater than 200,000 Da.

The elastomers for which the best metformin release profile was obtained are the triblock sequences copolymers marketed under the name KRATON G 1651®. This is particularly true when the elastomeric matrix is coated on one weave.

The elastomeric matrix advantageously comprises an elastomer content ranging from 2 to 15% by weight, preferably from 3 to 12% by weight, in relation to the total weight of the elastomeric matrix.

Metformin

In addition to the elastomer, the elastomeric matrix implemented in the interface layer of the dressing according to the present invention comprises metformin having a particle size defined by a d50<300 μm and a d90<600 μm, the salts and the complexes thereof.

Metformin is an oral antidiabetic of the normoglycemic biguanide family used in the treatment of type-2 diabetes. Its role is to decrease the insulin resistance of the carbohydrate-intolerant organism and to decrease hepatic neoglucogenesis. The mode of administration of metformin is through the bone. Metformin is absorbed on the small intestine, circulates in the blood in a non-fixed manner and is excreted, unchanged, by the kidneys. Its mechanism of action is complex and is not to date fully elucidated. Metformin is a normoglycemic: it does not act on the secretion of insulin, or on the sensitivity of insulin of glucose-using tissues (muscles, adipose tissue). Metformin also has a role in inhibiting neoglucogenesis, by inhibiting mitochondrial glycerophosphate dehydrogenase, and in the membrane transport of glucose (decrease in the intestinal resorption thereof). It also increases the release of Glucagon-like peptide-1, inhibits the path of glucagon, increases the production of lactates by the enterocytes.

According to a preferred embodiment, the metformin implemented has the form of a metformin hydrochloride.

The particle size of the metformin, when it is calculated according to the Fraunhoffer optical model between 0.375 μm and 2,000 μm, measured with a laser with the dry powder module, responds to the following characteristics:

d50<300 μm, preferably d50<200 μm d90<600 μm, preferably d90<510 μm.

Preferably, in the framework of the present invention, the particle size distribution of the metformin is unimodal.

In the framework of the present invention, the quantities of metformin introduced into the dressings are from 0.5 to 15% by weight, preferably 1 to 10% by weight, in relation to the total weight of the elastomeric matrix.

The quantity of metformin implemented is adapted according to the release kinetics sought. Advantageously, it is provided that the interface layer comprises from 0.01 to 4.0 mg/cm$^2$, preferably from 0.1 to 2.5 mg/cm$^2$, advantageously from 0.1 to 1.8 mg/cm$^2$ of metformin. This value is brought in relation to the active surface of the interface layer, i.e. the surface intended for releasing the active principle par opposition to the non-active portions of the dressing, also called "pavement", which generally allow for the fastening of the latter around the zone to be treated.

In the framework of its use in a dressing, the metformin is incorporated in a quantity such that the percentage of metformin released after 72 hours is between 40 and 100% of the quantity of metformin inserted in the dressing.

In the framework of its use in a dressing, the metformin is incorporated in a quantity such that the percentage of metformin released after 24 hours is between 25 and 60% of the quantity of metformin inserted in the dressing.

In the framework of its use in a dressing, the metformin is incorporated in a quantity such that the percentage of metformin released after 4 hours is between 10 and 40% of the quantity of metformin inserted in the dressing.

Releasing Agent

In order to favour the release of metformin, the elastomeric matrix according to the invention can also include a releasing agent.

According to a preferred embodiment, in order to allow for the controlled release of the metformin, the releasing agent is chosen from the copolymer of the salt of 2-methyl-2[(1-oxo-2-propenyl)amino]-1-propanesulfonic acid and of 2-hydroxyethyl ester of propenoic acid or from the mixture of 2-octyl-1-dodecanol, D-xylopyranoside, 2-octyldodecyl and of polyethyleneglycol 30 dipolyhydroxystearate.

The copolymer of the salt of 2-methyl-2[(1-oxo-2-propenyl)amino]-1-propanesulfonic acid and of 2-hydroxyethyl ester of propenoic acid is for example marketed under the name SEPINOV EMT10® by the company SEPPIC.

The mixture of 2-octyl-1-dodecanol, D-xylopyranoside, 2-octyldodecyl and of polyethyleneglycol 30 dipolyhydroxystearate is for example marketed under the trade name EASYNOV® by the company SEPPIC.

The releasing agent is present in a quantity ranging from 0.01 to 10% by weight, preferably 0.05 to 5% by weight, in relation to the total weight of the elastomeric matrix.

According to a preferred embodiment, when the copolymer of the salt of 2-methyl-2[(1-oxo-2-propenyl)amino]-1-propanesulfonic acid and of 2-hydroxyethyl ester of propenoic acid is used as a releasing agent, it is more preferably implemented in a quantity ranging from 0.01 to 1.9%, preferably 0.05 to 1.5%, more preferably from 0.1 to 1% by weight, in relation to the total weight of the elastomeric matrix.

Hydrocolloid

The elastomeric matrix can also include at least one hydrocolloid.

The term hydrocolloid or hydrocolloid particles here designates any compound normally used by those skilled in the art for its aptitude to absorb aqueous liquids such as water, physiological serum or the exsudates of a wound.

The term hydrocolloids means any suitable hydrocolloid compound, such as for example, pectin, alginates, natural vegetable gums (Karaya gum), cellulose derivatives such as carboxymethylcelluloses (CMC) and the alkaline metal salts thereof (the sodium or calcium salts of carboxymethylcellulose known under the reference of CMC Blanose 7H4XF®), as well as synthetic polymers with a base of superabsorbent acrylic acid salts, such as among others the products marketed by the company BASF® under the name Luquasorb 1003®, or by the company CIBA Speciality Chemicals® under the name Salcare SC91®, as well as mixtures of these compounds. These hydrocolloids are advantageously implemented in the form of particles for the preparation of the adhesive composition.

The hydrocolloids preferred in the framework of the present invention are the alkaline metal salts of carboxymethylcellulose, and in particular sodium carboxymethylcellulose.

The size of the hydrocolloid particles is advantageously between 50 and 100 microns, in particular about 80 microns.

The quantity of hydrocolloids incorporated into the elastomeric matrix can advantageously range from 1 to 25% by weight, more preferably from 10 to 20% by weight, and even more preferably from 12 to 16% by weight, in relation to the total weight of the elastomeric matrix.

The Plasticiser

According to a preferred embodiment, the elastomer can be plasticised by adding an oily element that makes it possible to obtain a highly cohesive and elastic gel with a fatty appearance.

In the framework of the present invention, the choice of an oily element is more preferably a mineral oil that has both good compatibility with the elastomers described hereinabove and a recognised tolerance with respect to tissues of the skin. Preference will be given to the use of paraffin oils more preferably with low viscosities or mixtures of paraffin oil and of officinal vaseline will preferably be used.

According to an alternative of the present invention, a mineral oil combined with a small quantity of vegetable oil can also be used.

Among the plasticising oils that are particularly suitable, mention can be made of the products marketed by the company SHELL under the names ONDINA® and RISELLA® which are comprised of mixtures with a base of naphthenic and paraffinic compounds or by the company Hansen & Rosenthal under the names Pionier® or by the company ExxonMobil under the names Marcol® or by the company Petro Canada under the names Puretol®, or encore by the company Sonneborn under the name Blandol®.

More preferably white mineral oils will be used such as the oil marketed by the company Hansen & Rosenthal under the name Pionier 2076 P®.

According to a preferred embodiment, the plasticiser is a mixture of mineral oil, preferably paraffin oil with vaseline, preferably from 50 to 98% by weight of paraffin oil and from 2 to 15% by weight of vaseline.

Tackifying Resin

The elastomeric matrix can also include at least one tackifying resin in order to provide them with an adhesive nature that facilitates the positioning thereof on the wound.

The tackifying resins that can optionally enter into the composition of the elastomeric matrices according to the invention are chosen in particular from polyisobutylenes with a low molecular weight. Generally, the use of hydrogenated resins is preferred such as the Escorez® resins in the series 5000, and even more preferably, the Escorez 5380® resin.

Antioxidants

The elastomeric matrix can furthermore include, one or several antioxidant agents.

The term "antioxidant" means any molecule that decreases or prevents the oxidation of other chemical substances. The antioxidant can be chosen from the phenolic antioxidants, such as for example the products marketed by the company CIBA-GEIGY® under the name Irganox 1010®, Irganox 565® and Irganox 1076® as well as sulphur-containing antioxidants, such as for example zinc dibutyldithiocarbamate marketed by the company AKZO® under the name PERKACIT ZDBC®. Preferably, the antioxidant used will be Irganox 1010®.

In the framework of the present invention, preference will be given to the use of the IRGANOX 1010® product.

These antioxidants can be used in a quantity of about from 0.05 to 1% by weight, more preferably from 0.1 to 0.5% by weight, in relation to the total weight of the elastomeric matrix.

Additional Active Substances

In addition to metformin, the elastomeric matrix can include one (or several) other active substances that make it possible to induce or accelerate the healing or that are able to have a favourable role in treating a wound.

Among these active substances, mention can be made of, in particular, by way of examples:
- agents favouring healing such as retinol, vitamin A, vitamin E, N-Acetyl Hydroxyproline, Centella Asiatica extracts, papain, silicone, essential oils of thyme, niaouli, rosemary, sage, hyaluronic acid, potassium octasulphate sucrose, sucralfate, allantoin
- antibacterial agents such as silver salts or complexes (such as silver sulphates, silver nitrates, silver sulphamides or encore zeolites with a silver base), zinc or copper salts, metronidazole, neomycin, penicillins, clavulanic acid, tetracyclines, mynocycline, chlortetracycline, aminoglycosides, amikacin, gentamicin, probiotics;
- antiseptics such as chlorhexidine, triclosan, biguanide, hexamidine, thymol, lugol, povidone-iodine, benzalkonium and benzethonium chloride;
- painkillers such as paracetamol, codeine, dextropropoxyphene, tramadol, morphine and the derivatives thereof, corticoids and the derivatives thereof;
- local anaesthetics such as lidocaine, benzocaine, dibucaine, pramoxine hydrochloride, bupivacaine, mepivacaine, prilocaine, etidocaine;
- anti-inflammatories such as non-steroidal anti-inflammatory drugs (NSAIDs), aspirin or acetylsalicylic acid, ibuprofen, ketoprofen, flurbiprofen, diclofenac, aceclofenac, ketorolac, meloxicam, piroxicam, tenoxicam, naproxen, indometacin, naproxcinod, nimesulide, celecoxib, etoricoxib, parecoxib, rofecoxib, valdecoxib, phenylbutazone, niflumic acid, mefenamic acid;

Of course, the polymeric matrix implemented according to the invention can also include one or several other compounds known for their action in the detersion phase such as for example:
- enzymes;
- urea.

Advantageously, the elastomeric matrix implemented in the present application in particular comprises the following elements:
- at least one elastomer,
- metformin, the salts or the complexes thereof,
- at least one hydrocolloid,
- at least one releasing agent chosen from the copolymer of the salt of 2-methyl-2[(1-oxo-2-propenyl)amino]-1-propanesulfonic acid and of 2-hydroxyethyl ester of propenoic acid or of the mixture of 2-octyl-1-dodecanol, D-xylopyranoside, 2-octyldodecyl and polyethyleneglycol 30 dipolyhydroxystearate,
- at least one plasticising oil and
- possibly at least one tackifying resin.

According to a more preferred embodiment, the elastomeric matrix consists substantially:
- 0.5 to 15%, preferably 1 to 10% by weight, in relation to the total weight of the matrix, metformin, the salts or the complexes thereof;
- 2 to 15%, preferably 3 to 12% by weight, in relation to the total weight of the matrix, of at least one elastomeric polymer;
- 1 to 25%, preferably 10 to 20% by weight, in relation to the total weight of the matrix, of at least one hydrocolloid;
- 45 to 95%, preferably 50 to 85% by weight, in relation to the total weight of the matrix, of at least one plasticiser;
- 0.05 to 1%, preferably 0.1 to 0.5% by weight, in relation to the total weight of the matrix, of at least one agent antioxidant;
- 0.01 to 10%, preferably 0.05 to 5% by weight, in relation to the total weight of the matrix, of a releasing agent chosen from the copolymer of the salt of 2-methyl-2 [(1-oxo-2-propenyl)amino]-1-propanesulfonic acid and of 2-hydroxyethyl ester of propenoic acid or the mixture of 2-octyl-1-dodecanol, D-xylopyranoside, 2-octyldodecyl and polyethyleneglycol 30 dipolyhydroxystearate.

According to an even more preferred embodiment, the elastomeric matrix consists substantially:
- 0.5 to 15%, preferably 1 to 10% by weight, in relation to the total weight of the matrix, metformin, the salts or the complexes thereof;
- 2 to 15%, preferably 3 to 12% by weight, in relation to the total weight of the matrix, of at least one elastomeric polymer;
- 1 to 25%, preferably 10 to 20% by weight, in relation to the total weight of the matrix, of at least one hydrocolloid compound;
- 45 to 95%, preferably 50 to 85% by weight, in relation to the total weight of the matrix, of at least one plasticiser;
- 0.01 to 10%, preferably 0.05 to 5% by weight, in relation to the total weight of the matrix, of a releasing agent chosen from the copolymer of the salt of 2-methyl-2 [(1-oxo-2-propenyl)amino]-1-propanesulfonic acid and of 2-hydroxyethyl ester of propenoic acid or the mixture of 2-octyl-1-dodecanol, D-xylopyranoside, 2-octyldodecyl and polyethyleneglycol 30 dipolyhydroxystearate.

In the framework of the present invention, the elastomeric matrix can be coated on one weave in order to form the interface layer, or moulded by hot casting, for example on a plate, then demoulded in order to obtain a self-supported interface dressing.

Weave

The term "weave" means a structure that, in the framework of the present invention, can be comprised of any perforated material such as a perforated film, a thermoplastic net, a woven, a knit or a non-woven, preferably elastic for better maintaining of the dressing on the skin. The materials forming the weave are preferably polymeric such as a polyamide, polyurethane, polyester, polyether, polyvinyl chloride, polyvinylidene chloride, polyvinyl alcohol, polyvinyl acetate, polystyrene, polyvinyl fluoride, a polyolefin such as for example a polyethylene or a polypropylene, a material with a base of polyether polyester copolymer, polyester or polyether polyurethane copolymer, polyether polyamide copolymer.

The weave can be formed from a fabric of threads made of flexible material. This weave has the form of a fabric with a wide open mesh and can be obtained by weaving and knitting methods that make it possible to form open meshes of a regular size, square or polygonal. In the case of weaving, the meshes can be fixed by means of doup threads in order to obtain good dimensional stability. The dimension of the meshes is such that the unit surface of the openings is about from 0.5 to 10 mm$^2$, preferably 0.5 to 3 mm$^2$, the rate of opening of a fabric (ratio of the open surface over the total surface) being about from 50 to 90%. The thread used to manufacture the fabric is preferably continuous yard. The term continuous yarn means a thread formed from one or several long twisted filaments; choosing long filaments makes it possible to avoid short fibres that risk become detached from the support and dispersing near the contact surface with the wound. For the same reason, the material that the threads are comprised on is more preferably of the hydrophobic type, of an artificial or synthetic nature; these components, such as for example polyesters, polyamides, cellulose acetates make it possible to obtain long filaments and threads that have much less fibrils than the threads obtained using short fibres for example. Choosing certain synthetic materials such as polyesters also gives the possibility of heat-setting the wide mesh structure of the support. The fabric with wide meshes is preferably produced with threads of the same nature, but it is possible to use fabrics produced for example with warp threads and weft threads which would be of a different nature. The nature of the thread is, for example, a polyester of the polyethylterephthalate type, polyamide or an acetate of cellulose; more preferably a fabric with wide heat-set meshes with continuous polyester threads (Tergal or polyethylterephthalate) is used, for example fabrics marketed under the name of marquisette, with a weight of about 20 to 80 g/m 2. In the framework of the present invention, preferably one weave will be used such as described in patent EP 2 793 773.

Coating of the Weave with the Elastomeric Matrix or Moulding of the Elastomeric Matrix In order to control the release profile of the metformin, the elastomeric matrix can be coated on the weave described hereinabove. The elastomeric matrix can also be moulded by hot casting then demoulded once cooled in order to obtain a self-supporting interface dressing.

The coating can be carried out by any method known to those skilled in the art.

The method of coating the weave with the polymeric matrix must make it possible to imprison well the threads of the weave in the matrix, while leaving most of the non-closed off openings by the polymeric matrix.

According to the structure of the support used, the quantity of polymeric matrix used will be approximately 50 to 300 g/m$^2$, and preferably 60 to 160 g/m$^2$. In the case of a self-supported interface dressing, the quantity of polymeric matrix used will be approximately 250 to 600 g/m$^2$. In light of the components of the polymeric matrix, the coating is carried out hot, without solvent, according to a continuous method in which the weave strip is passed in a bath of melted polymeric matrix at 140-150° C.; the weave strip covered with melted gel is then passed between two fixed cylinders pressed against one another with a predetermined separation in such a way as to remove the excess polymeric matrix. The quantity of polymeric matrix remaining on the weave primarily depends on the separation imposed between then fixed cylinders. The covered weave is then cooled.

The interface layer thus obtained is more preferably non-adherent. Once cooled, it can then be covered with two protective films, for example thin films made of polyester. Due to the non-adherent nature of the interface layer, these films do not require any anti-adherent treatment and have for function only to facilitate the extraction from the main packaging and the handling during the setting in place on the wound. The interface layer is then cut into individual interface dressings according to the dimensions suited for use, packaged in sealed and sterile sachets.

The interface layer according to the invention can be used in a manner similar to the currently known interfaces such as for example Tulle Gras Lumière. Conventionally, the compress is placed in direct contact with the wound and can be used as single layer or multiple layers: the flexibility of the weave and of the polymeric matrix makes it possible to apply the interface layer well over the entire surface of the wound, by overflowing onto the perimeter to the healthy skin.

Dressing

The dressing according to the invention comprises at least one interface layer such as described hereinabove, intended to be placed in contact with the wound. The term dressing thus means, in terms of the present invention, any medical device comprising an elastomeric matrix such as described hereinabove, intended to be placed in contact with the wound.

Such dressings are in particular used for the treatment of wounds. The choice of the dressing depends on the type of lesion to be treated. For example, absorbent dressings are favoured in the case of treating exuding wounds.

Absorbent Layer

The interface layer can for example be covered with an absorbent layer if the wound is highly exudative.

The term absorbent layer means in terms of the present invention any material or combination of materials used for producing an absorbent layer in the field of dressings or hygiene products, such as diaper pants.

Among these materials, mention can be made of hydrophilic absorbent foams, for example with a polyurethane base, textile materials in particular wovens and non-wovens with a base of absorbent fibres or gelling fibres, superabsorbent materials for example with an acrylic polymer base in particular in the form of particles or fibres, compositions more preferably adhesive containing particles of hydrocolloids and hydrogels.

By way of example of an absorbent layer, mention can be made of the foams marketed by the companies CORPURA and RYNEL respectively under the references MCF03 and L 00562-B.

The absorbent layer can also be formed from non-wovens with a cellulose fibre base. These non-wovens can also incorporate particles of superabsorbent polymers commonly designated under the term SAP such as acrylic polymers (sodium polyacrylates) in a proportion between 10 and 60% by weight of the total weight of the compress in order to increase their absorption capacity. Likewise, in order to favour the integrity of the non-woven during the absorption, the absorbent fibres can be combined with non-absorbent fibres such as heat-bonded fibres or bonded together using a latex such as an EVA latex. All of these absorbent non-wovens are well known to those skilled in the art and designated under the terms of "hybrid bonded" or "multi-bonded" airlaid (see for example WO95/30394 or WO94/10954).

Incidentally, a combination of different non-wovens mentioned hereinabove can be used as an absorbent layer.

Using non-wovens with a gelling fibre base is also well known to those skilled in the art. Mention can be made, by way of example, as gelling fibres the fibres with a base of hyaluronic acid, chitosan, collagen, pectin, alginates, sodium carboxymethylcellulose, sodium carboxymethylcellulose combined with alginates, chemically-modified cellulose fibres, in particular carboxymethylated, or fibres with a super-absorbent polymer base. By way of example, mention can be made of the fibres marketed under the names Lanseal F.

As hereinabove these gelling fibres can be combined with other types of fibres in order to improve the properties of the non-wovens such as for example heat-bonded fibres. Such non-wovens and the various fibres that can be comprised of are described for example in the following patent applications: WO 2007/025546, WO 2007/08531, WO 93/12275, WO 00/01425, WO 94/16746, WO 95/19795, EP 878 204, EP 1 435 247 or WO 86/01400.

The term super-absorbent here means polymers in the form of powders, fibres or any other form that gels when in contact with biological liquids.

Hydrophilic polymers in the form of particles having super-absorbent properties are described for example in applications U.S. Pat. No. 4,102,340. In particular absorbent materials such as crosslinked polyacrylamides are used for this. Preferred super-absorbent particles are comprised of partially neutralized crosslinked polyacrylic acid. Mention can be made by way of example the products marketed by the company BASF under the name LUQUASORB or those marketed by the company Ciba Speciality Chemicals under the name SALCARE.

These super-absorbents are generally used in combination with cellulose fibres as described hereinabove or incorporated into compositions that are preferably adhesive used in hydrocolloid dressings.

The absorbent layer can also be comprised of these super-absorbents, alone or incorporated between 2 distribution layers, or with a non-woven of absorbent fibres such as for example cellulose or viscose fibres (see EP 358412 or U.S. Pat. No. 6,096,942).

Adhesive Maintaining Strip

The interface layer and the possible absorbent layer can be maintained in place by a strip or an adhesive support intended to be fastened onto the peripheral zones of healthy skin far from the wound. In this case, the interface layer can be chosen in such a way that the dressing has an adhesive power on a steel plate between 0.5 and 100 cN/cm, preferably between 5 and 40 cN/cm. This adhesive power is measured according to the method EN 1939 in which a sample of dressing 20 mm wide and 150 mm long is placed on a steel plate and wherein, after 10 minutes, the adhesive power is measured with a dynamometer at a traction speed of 100 mm/min with an angle of 90°.

The dressing thus produced can remain in place for an extended period of time: indeed, the highly cohesive polymeric matrix does not disintegrate and the presence of a small quantity of hydrocolloids maintains a degree of humidity on the surface of the wound that is sufficient to prevent the latter from drying out. In addition, due to the non-adherent nature of the polymeric matrix used, it is possible, practically without any risk, to remove the absorbent pad that does not adhere to the gel without moving the sterile interface layer, in order to change the development of the wound. Although the interface layer is translucent, which allows for an examination of the wound by transparency, it may also be necessary to remove this interface layer in order to conduct a more precise visual inspection or to proceed with a direct drug treatment on the zone in the process of healing: this removal is done easily without pain and without damaging the newly regenerated tissues because the polymeric matrix does not adhere to the surface of the wound, or to the surrounding skin. In addition, due to a strong cohesion of the polymeric matrix wherein the threads of the fabric are imprisoned and the presence of CMC that maintains a slightly humid environment, the removal of the interface layer can be done completely, without leaving any particles or fatty bodies such as occurs with certain products that are currently on the market. Cleaning the wound is consequently clearly facilitated. With all of these advantages which are excellent cohesion combined with a non-adherent nature on a wet surface and on dry skin, the best conditions favourable for the healing process of the wound are brought together.

The dressings that are suitable for the present invention can be any commercially available dressing to which the interface layer described hereinabove intended to be placed in contact with a wound is associated.

Mention can be made, as examples of commercial dressings to which the interface layer according to the invention can be associated:

Polyurethane films, such as for example the products marketed by the company Smith&Nephew under the brand Opsite®, or by the company 3M under the brand Tegaderm® or by Laboratoires URGO under the brand Optiskin®. These dressings are comprised of a thin transparent film (about 20 to 50 µm) of adhesive polyurethane. Their transparency allows for a visual control of the zone to be treated. These polyurethane films are semi-permeable, they are permeable to gaseous exchanges, and are impermeable to liquids and to bacteria. They provide a mechanical protection with regards to the phenomena of rubbing, friction and shearing;

Hydrocellular dressings, such as for example the products marketed by Mölnlycke under the brand Mepilex® or by Smith & Nephew under the brand Allevyn®, or by Laboratoires URGO under the brand Cellosorb®. These dressings are generally formed from a support which can be a polyurethane film or a non-woven, of an absorbent layer which can be a polyurethane foam. The face intended to come into contact with the wound of this absorbent layer can be covered with a mass of adherent coating or not. These dressings have a high absorption capacity, via capillarity and/or via retention within the hydrocellular structure;

Hydrofibre dressings, such as for example the products marketed by Convatec under the brand Aquacel®. These dressings are non-woven fibres of pure hydrocolloids (carboxymethylcellulose sodium). These dressings are very hydrophilic and are transformed into a cohesive gel in contact with exsudates. They have a very high absorption capacity and also make it possible to "trap" bacteria, thus controlling bacterial contamination;

Alginates, such as for example the products marketed by Smith & Nephew under the brand Algisite® or by Coloplast under the brand Seasorb® soft or by Laboratoires URGO under the brand Urgosorb®. These dressings generally have the form of compresses or of gauzes. They are comprised of natural polysaccharides and gel in contact with exsudates. They have a very high absorption capacity and can also "trap" bacteria, thus controlling bacterial contamination.

Method for Producing a Dressing and Use

The present invention also has for subject matter a method for producing a dressing such as described hereinabove, characterised in that it comprises:

1. the preparing of an interface layer formed from an elastomeric matrix by:
   i. preparing an elastomeric matrix by dispersion of the metformin having a particle size defined by a d50<300 µm and a d90<600 µm, the salts and the complexes thereof in an elastomer, ii. the coating of a weave with the elastomeric matrix prepared in the step i or the hot casting of said matrix, preferably on an engraved plate forming for example the imprint of a net or grid with a square mesh.

2. optionally the covering of the interface layer with at least one absorbent layer
3. optionally the maintaining of the interface layer and of the possible absorbent layer by a strip or an adhesive support intended to be fastened onto the peripheral zones of healthy skin far from the wound.

The subject matter of the invention is also the use of a dressing such as described hereinabove, for the healing of wounds, as well as a dressing such as described hereinabove for the use thereof for the healing of wounds.

The following examples show, in a non-limiting way, the invention that is the subject matter of the present application.

Generally, the various exemplified dressings were prepared according to the following method:

The carboxymethylcellulose and the metformin are premixed and screened at 315 µm.

The vaseline and half of the oil are introduced into a mixer at a temperature setting of 115° C., at a speed from 75 to 120 rotations per minute (rpm), then the carboxymethylcellulose powders and screened metformin are introduced. This is mixed for 15 minutes.

The temperature setting is increased to 150° C. Then half of the oil, the elastomer and the antioxidant are introduced. This is mixed for 40 minutes (until a smooth and homogeneous mixture is obtained). The releasing agent is introduced 15 minutes before the end.

Then the tank of the mixer is emptied.

Interface dressings comprised of a weave (or marquisette) (weave 601 marketed by the company MDB TEXINOV) coated with elastomeric matrix were elaborated using elastomeric matrices of the examples 1 to 21.

The example 22 was carried out by hot casting of the composition described in table 23 on an etched plate forming the imprint of a net or grid with a square mesh that has the following dimensions: 200×200 mm, lugs of 1×1 mm, grooves d=600 µm, l=1.6 mm. This moulding is followed by a demoulding. The elastomeric matrix thus obtained does not have any support weave and forms a self-supported interface layer.

Method for Measuring the Cumulative and Non-Cumulative Release of Metformin:

Equipment

Luna SCX column 5 µm-100 Å-100 mm×4.6 mm, ref. Phenomenex 00D-4398-E0,

HPLC system provided with a UV detector, a sample changer and a column over,

Reagents

Ammonium dihydrogen phosphate for analysis. For example: ref. VWR 21305.290 or equivalent, Low UV acetonitrile for analysis. For example: ref. VWR 20048.290 or equivalent, Sodium chloride for analysis. For example: ref. VWR 27810.295 or equivalent, Purified water, HPLC quality.

Reference Substance

Metformin hydrochloride for secondary reference stored in a closed bottle stored in drying oven.

Solutions/Samples to be Prepared

Phase Mobile

The phase mobile is a solution of ammonium dihydrogen phosphate at 17 g/L to which are added 2% acetonitrile.

Test Solutions

Preliminary precaution: the physiological serum used during the analysis will be thermostatically controlled beforehand at 32° C.

Cut a sample of 5 cm×5 cm at the centre of the dressing (weigh the sample),

Introduce the sample into a hermetic jar,

Add 10.0 mL of physiological serum,

Stir at 120 strokes/minutes at 32° C. for 72 h,

Take 1 sampling per jar at 4 h, 7 h, 24 h, 48 h and 72 h:

At each one of these points, recover the supernatant,

Place 10.0 mL of physiological serum in each jar,

Stir again until the next sampling point.

Assay the test solution by HPLC-UV.

Operating Conditions

TABLE 1

Chromatographic conditions

| | |
|---|---|
| Column | Luna SCX - 5 µm - 100 mm × 4.6 mm |
| Phase mobile | Ammonium dihydrogen phosphate at 17 g/L + 2% of acetonitrile |
| Flow rate | 1.2 mL/min |

TABLE 1-continued

| Chromatographic conditions | |
|---|---|
| Temperature of the sample changer | Non-refrigerated and not temperature monitored |
| Temperature of the column oven | 35° C. |
| Mode | Isocratic |
| Injection volume | 10 μL |
| Detection | UV set to 232 nm |
| Retention time of the metformin peak | Approximately 6 minutes |
| Analysis time | 10 minutes |

Calculations/Expression of Results

Determination of the quantity of metformin released over time (either as a %, or in μg/cm²).

Listing of HPLC data

The test solutions analysed are quantified in relation to the calibration line. The results obtained from the calculator are given in μg/mL and are listed in table 2. The identification of the various tests is also indicated as follows:

Surface of the sample: S (cm²)

Weight of the weave: G (g/m²)

Metformin content in the matrix: T (%)

Initial volume: V (mL)

TABLE 2

| | | | DRY raw results (μg/mL) | | | | | |
|---|---|---|---|---|---|---|---|---|
| Sample no. | Reference | Total mass (g) | Coated mass (g) | 4 h | 7 h | 24 h | 48 h | 72 h |
| Pst X | EXXXX | m | | a | b | c | d | e |

With:

a, b, c, d, e=HPLC raw results corresponding to the concentration of the test solutions injected respectively at 4 h, 7 h, 24 h, 48 h and 72 h (expressed in μg/mL to the nearest $10^{-4}$)

Coated mass:

$$\text{Coated mass} = \left[\text{total mass} - \left(\frac{S}{10000} \times G\right)\right]$$

$S$ = surface of the sample (cm²)

$G$ = weight of the weave (g/cm²). In the case of these dressings, the weight $G$ of the weave is 28 g/m².

Calculations of the Results of Cumulative Release

The cumulative release results at each sampling point are expressed in μg/cm² and as a percentage (%).

TABLE 3

| Sample | | Cumulative release of metformin in μg/cm² | | | | | |
|---|---|---|---|---|---|---|---|
| no. | Reference | 0 | 4 h | 7 h | 24 h | 48 h | 72 h |
| Pst X | EXXXX | 0.00 | A μg/cm² | B μg/cm² | C μg/cm² | D μg/cm² | E μg/cm² |

TABLE 4

| Sample | | Cumulative release of metformin in % | | | | | |
|---|---|---|---|---|---|---|---|
| no. | Reference | 0 h | 4 h | 7 h | 24 h | 48 h | 72 h |
| Pst X | EXXXX | 0.00 | A % | B % | C % | D % | E % |

With:

A μg/cm², B μg/cm², C μg/cm², D μg/cm² and E μg/cm² which respectively designate the cumulative release at 4 h, 7 h, 24 h, 48 h and 72 h in μg/cm² (to the nearest $10^{-2}$).

A %, B %, C %, D % and E % which respectively designate the cumulative release at 4 h, 7 h, 24 h, 48 h and 72 h in % (to the nearest $10^{-1}$).

TABLE 5

| Expression of the results in μg/cm² Cumulative release in μg/cm² | | |
|---|---|---|
| Time | Symbol | Calculation formula |
| 4 h | A μg/cm² | $\frac{a \times V}{S}$ |
| 7 h | B μg/cm² | $\frac{b \times V}{S} + A$ μg/cm² |
| 24 h | C μg/cm² | $\frac{c \times V}{S} + B$ μg/cm² |
| 48 h | D μg/cm² | $\frac{d \times V}{S} + C$ μg/cm² |
| 72 h | E μg/cm² | $\frac{e \times V}{S} + D$ μg/cm² |

TABLE 6

| Expression of the results in % Cumulative release in % | | |
|---|---|---|
| Time | Symbol | Calculation formula |
| 4 h | A % | $\frac{a \times V}{\frac{T}{100} \times \text{coated mass} \times 1000000} \times 100$ |
| 7 h | B % | $\frac{b \times V}{\frac{T}{100} \times \text{coated mass} \times 1000000} \times 100 + A$ % |
| 24 h | C % | $\frac{c \times V}{\frac{T}{100} \times \text{coated mass} \times 1000000} \times 100 + B$ % |
| 48 h | D % | $\frac{d \times V}{\frac{T}{100} \times \text{coated mass} \times 1000000} \times 100 + C$ % |
| 72 h | E % | $\frac{e \times V}{\frac{T}{100} \times \text{coated mass} \times 1000000} \times 100 + D$ % |

Calculations of the Non-Cumulative Release Results:

It is sufficient to use the cumulative release results and to subtract the value obtained at time t from the value obtained at time t−1.

Cumulative Release Results:

TABLE 7

| Sample no. | Reference | Cumulative release of metformin in µg/cm² | | | | | |
|---|---|---|---|---|---|---|---|
| | | 0 | 4 h | 7 h | 24 h | 48 h | 72 h |
| Pst X | EXXXX | 0.00 | A µg/cm² | B µg/cm² | C µg/cm² | D µg/cm² | E µg/cm² |

TABLE 8

| Sample no. | Reference | Cumulative release of metformin in % | | | | | |
|---|---|---|---|---|---|---|---|
| | | 0 h | 4 h | 7 h | 24 h | 48 h | 72 h |
| Pst X | EXXXX | 0.00 | A % | B % | C % | D % | E % |

Use of these Results to Express the Non-Cumulative Release:

TABLE 9

| Sample no. | Reference | Non-cumulative release of metformin in µg/cm² | | | | | |
|---|---|---|---|---|---|---|---|
| | | 0 | 4 h | 7 h | 24 h | 48 h | 72 h |
| Pst X | EXXXX | 0.00 | A µg/cm² | B µg/cm²-A µg/cm² | C µg/cm²-B µg/cm² | D µg/cm²-C µg/cm² | E µg/cm²-D µg/cm² |

TABLE 10

| Sample no. | Reference | Non-cumulative release of metformin in % | | | | | |
|---|---|---|---|---|---|---|---|
| | | 0 h | 4 h | 7 h | 24 h | 48 h | 72 h |
| Pst X | EXXXX | 0.00 | A % | B %-A % | C %-B % | D %-C % | E %-D % |

List of the Results

All of the results will be listed in summary tables such as those described hereinabove, the release kinetics of the metformin is then plotted as a function of time (expressed in hours).

Examples 1 to 7

TABLE 11

| Commercial ref | Ex. 1 % by weight | Ex. 2 % by weight | Ex. 3 % by weight | Ex. 4 % by weight | Ex. 5 % by weight | Ex. 6 % by weight | Ex. 7 % by weight |
|---|---|---|---|---|---|---|---|
| SEBS (Kraton G1654 ES from Kraton Polymer) | 6 | 6 | 6 | 6 | 6 | 6 | 6 |
| White mineral oil (Ondina 919 from Shell) | 64.88 | 64.88 | 64.88 | 64.88 | 64.88 | 64.88 | 64.88 |
| Pentacrythitol Tetrakis3-(3,5-di-tert-butyl-4-hydroxyphenyl)propionate (Irganox 1010 from BASF) | 0.12 | 0.12 | 0.12 | 0.12 | 0.12 | 0.12 | 0.12 |
| Vaseline (Vaseline Codex A from Synteal) | 5 | 5 | 5 | 5 | 5 | 5 | 5 |
| Sodium carboxymethyl cellulose (CMC Blanose 7H4XF from Aschland) | 14 | 14 | 14 | 14 | 14 | 14 | 14 |
| Metformin from Fukang | 5 | 5 | 5 | 5 | 5 | 5 | 5 |
| copolymer of the salt of 2-methyl-2[(1-oxo-2-propenyl)amino]-1-propanesulfonic acid and of 2-hydroxyethyl ester of propenoic acid (Sepinov EMT 10 from SEPPIC) | 5 | | | | | | |
| Polyacrylate crosspolymer-6 (Sepimax Zen from SEPPIC) | | 5 | | | | | |
| octyldodecanol, octyldodecyl xyloside and PEG30 dipolyhydroxystearate (Easynov from SEPPIC) | | | 5 | | | | |
| Polysorbate 80 (Montanox 20 from SEPPIC) | | | | | 5 | | |
| Sorbitan Laurate (Montane 20 from SEPPIC) | | | | | | 5 | |

TABLE 11-continued

| Commercial ref | Ex. 1 % by weight | Ex. 2 % by weight | Ex. 3 % by weight | Ex. 4 % by weight | Ex. 5 % by weight | Ex. 6 % by weight | Ex. 7 % by weight |
|---|---|---|---|---|---|---|---|
| Acrylic Acid Polymer Sodium Salt, Additives (Aquakeep from Sumitomo Seika Chemicals) | | | | | 5 | | |
| Polyethylene glycol 300 | | | | | | | 5 |

TABLE 12

Average cumulative release of metformin in mg/cm$^2$

| | Average cumulative release in mg/cm$^2$ | | | |
|---|---|---|---|---|
| Examples | 0 h | 7 h | 24 h | 72 h |
| Example 1 | 0 | 0.23 | 0.34 | 0.41 |
| Example 2 | 0 | 0.31 | 0.40 | 0.44 |
| Example 3 | 0 | 0.20 | 0.29 | 0.36 |
| Example 4 | 0 | 0.48 | 0.59 | 0.62 |
| Example 5 | 0 | 0.51 | 0.59 | 0.61 |
| Example 6 | 0 | 0.34 | 0.43 | 0.47 |
| Example 7 | 0 | 0.43 | 0.52 | 0.56 |

TABLE 13

Average non-cumulative release of metformin in mg/cm$^2$

| | Average non-cumulative release in mg/cm$^2$ | | | |
|---|---|---|---|---|
| Examples | 0 h | 7 h | 24 h | 72 h |
| Example 1 | 0 | 0.23 | 0.11 | 0.07 |
| Example 2 | 0 | 0.31 | 0.08 | 0.05 |
| Example 3 | 0 | 0.20 | 0.09 | 0.06 |
| Example 4 | 0 | 0.48 | 0.10 | 0.03 |
| Example 5 | 0 | 0.51 | 0.09 | 0.02 |
| Example 6 | 0 | 0.34 | 0.09 | 0.04 |
| Example 7 | 0 | 0.43 | 0.09 | 0.04 |

Figure 1:
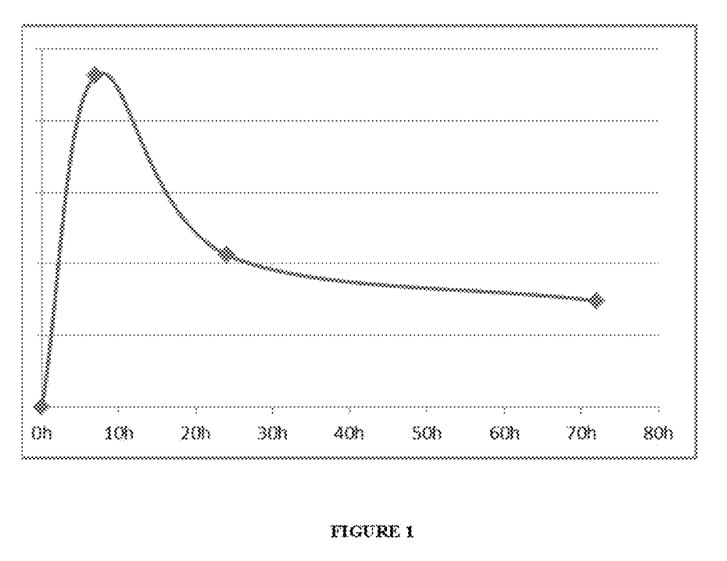
FIG. 1 is a graphical representation of the non-cumulative ideal dissolution profile and evaluated in mg/cm$^2$ of released active principle
Figure 2:
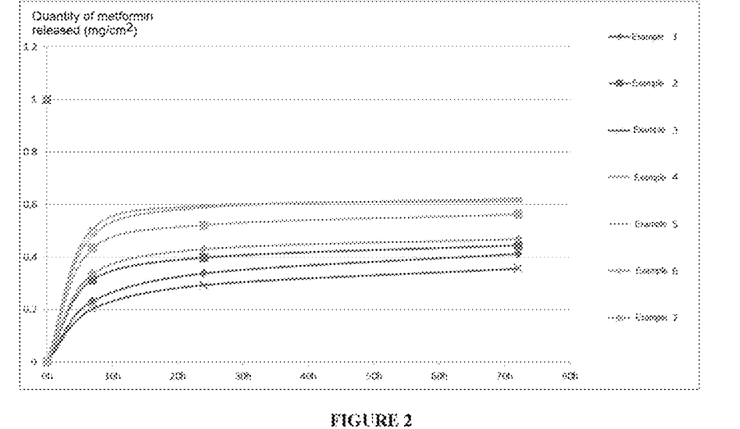
FIG. 2 is a graphical representation of the cumulative dissolution profiles, evaluated in mg/cm$^2$ of active principle released from dressings described from the example 1 to the example 7.

FIG. 2 is a graphical representation of the cumulative release of examples 1 to 7.

Figure 3:
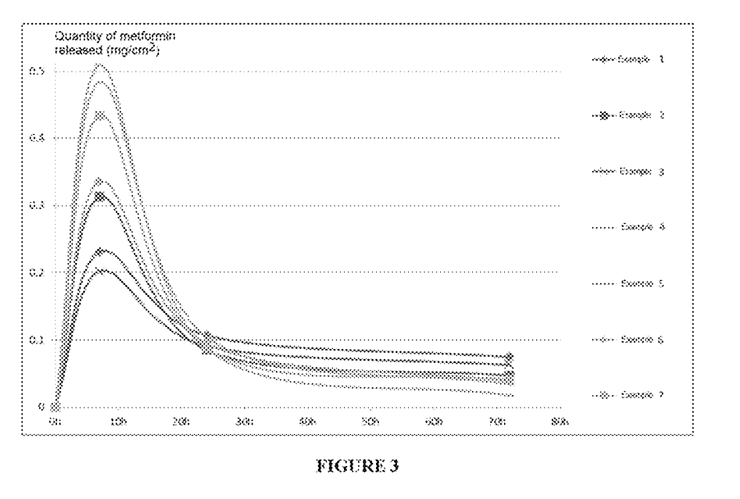
FIG. 3 is a graphical representation of the non-cumulative dissolution profiles, evaluated in mg/cm$^2$ of active principle released from dressings described from the example 1 and to the example 7.

FIG. 3 is a graphical representation of the non-cumulative release of examples 1 to 7.

The releasing agents that have the best kinetics and the best quantity released are SEPINOV EMT10® and Easynov®. They indeed allow for the best compromise between a release profile with a bolus and a slow and continuous release of the metformin, and a high total quantity of metformin released.

Examples 8 to 12

TABLE 14

| Commercial ref. | Ex. 8 % by weight | Ex. 9 % by weight | Ex. 10 % by weight | Ex. 11 % by weight | Ex. 12 % by weight |
|---|---|---|---|---|---|
| White mineral oil (Puretol 9P from Petro Canada) | 69.947 | 69.847 | 69.447 | 68.947 | 67.947 |
| SEBS (Kraton G1651 E from Kraton Polymer) | 4.931 | 4.931 | 4.931 | 4.931 | 4.931 |
| Pentacrythitol Tetrakis3-(3,5-di-tert-butyl-4-hydroxyphenyl)-propionate (Irganox 1010 from BASF) | 0.123 | 0.123 | 0.123 | 0.123 | 0.123 |
| Vaseline (Vaseline Codex A from Synteal) | 5 | 5 | 5 | 5 | 5 |
| Sodium carboxymethyl cellulose (CMC Blanose 7H4XF from Aschland) | 14.999 | 14.999 | 14.999 | 14.999 | 14.999 |
| Metformin from IPCA | 5 | 5 | 5 | 5 | 5 |
| copolymer of the salt of 2-methyl-2[(1-oxo-2-propenyl)amino]-1-propanesulfonic acid and of 2-hydroxyethyl ester of propenoic acid (Sepinov EMT 10 from SEPPIC) | 0 | 0.1 | 0.5 | 1 | 2 |

TABLE 15

Average cumulative release of metformin in μg/cm$^2$

| | Average cumulative release (μg/cm$^2$) | | | | | |
|---|---|---|---|---|---|---|
| Examples | 0 h | 4 h | 7 h | 24 h | 48 h | 72 h |
| Example 8 | 0.00 | 104 | 135 | 231 | 347 | 421 |
| Example 9 | 0.00 | 151.68 | 186.17 | 283.13 | 397.41 | 465.75 |
| Example 10 | 0.00 | 190.99 | 222.75 | 310.92 | 408.81 | 466.56 |
| Example 11 | 0.00 | 215.04 | 248.29 | 340.07 | 439.00 | 493.46 |
| Example 12 | 0.00 | 296.27 | 343.33 | 436.13 | 511.43 | 549.99 |

TABLE 16

Average non-cumulative release of metformin in μg/cm²

| Examples | Average non-cumulative release (μg/cm²) | | | | |
|---|---|---|---|---|---|
| | 0 h | 4 h | 7 h | 24 h | 48 h | 72 h |
| Example 8 | 0.00 | 104 | 31 | 96 | 116 | 74 |
| Example 9 | 0.00 | 151.68 | 34.49 | 96.96 | 114.28 | 68.33 |
| Example 10 | 0.00 | 190.99 | 31.76 | 88.17 | 97.89 | 57.75 |

TABLE 16-continued

Average non-cumulative release of metformin in μg/cm²

| Examples | Average non-cumulative release (μg/cm²) | | | | |
|---|---|---|---|---|---|
| | 0 h | 4 h | 7 h | 24 h | 48 h | 72 h |
| Example 11 | 0.00 | 215.04 | 33.25 | 91.77 | 98.94 | 54.45 |
| Example 12 | 0.00 | 296.27 | 47.07 | 92.80 | 75.29 | 38.56 |

Figure 4:
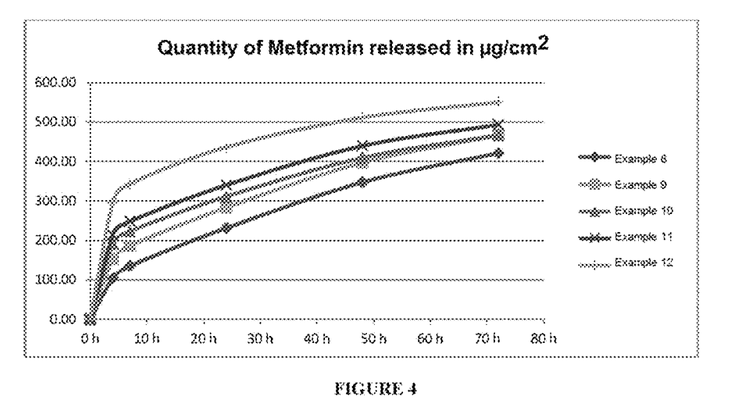
FIG. 4 is a graphical representation of the cumulative dissolution profiles, evaluated in µg/cm$^2$ of active principle released from dressings described from the example 8 to the example 12.

FIG. 4 is a graphical representation of the cumulative release of examples 8 to 12.

Figure 5:
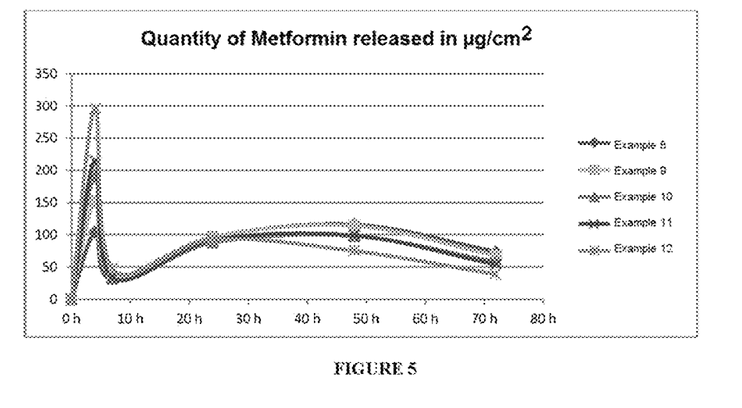
FIG. 5 is a graphical representation of the non-cumulative dissolution profiles, evaluated in µg/cm$^2$ of active principle released from dressings described from the example 8 to the example 12.

FIG. 5 is a graphical representation of the non-cumulative release of examples 8 to 12.

The rate of releasing agent, here Sepinov EMT 10, has an influence on the quantity of metformin released in 72 h. Indeed, the higher the rate of Sepinov EMT 10 is, the higher the quantity of metformin released is. This correlation is not however proportional. The non-cumulative results show that the quantity released at each sampling (4 h, 7 h, 24 h, 48 h, 72 h) depends on the rate of Sepinov EMT 10 contained in the matrix.

Thus, a rate of 2% of Sepinov EMT 10 will generate a more substantial release of metformin at 4 h while a lower rate of Sepinov EMT 10 (0.1%) will allow for a more progressive release over time.

Thus, the formulations at 0.1%; 0.5% and 1% of Sepinov EMT 10 (examples 9, 10 and 11) terminate their kinetics at 72 h with a similar released quantity but a profile that is somewhat different. In the framework of this application, a formulation that does not have a "flash" release is therefore preferred (excessive release at 4 h), and that has a most progressive release possible of metformin. The formulation that does not contain any releasing agent (example 8) has a progressive release profile but the quantity of metformin released is not as substantial that in the presence of a releasing agent, said quantity released could be insufficient in certain applications wherein a more substantial quantity of metformin should be released all throughout the use of the dressing.

Examples 13 to 16

TABLE 17

| Commercial ref. | Ex. 13 % by weight | Ex. 14 % by weight | Ex. 15 % by weight | Ex. 16 % by weight |
|---|---|---|---|---|
| White mineral oil (Puretol 9P from Petro Canada) | | | | 68 |
| White naphthenic oil (Pionier 2076P from Hansen&Rosenthal) | 71.74 | 66.74 | 68 | |
| SEBS (Kraton G1651 E from Kraton Polymer)[1] | | | 4.9 | 4.9 |
| SEBS (Kraton G1654 ES from Kraton Polymer)[1] | 6.34 | 6.34 | | |
| Pentacrythitol Tetrakis3-(3,5-di-tert-butyl-4-hydroxyphenyl)propionate (Irganox 1010 from BASF) | 0.12 | 0.12 | 0.12 | 0.12 |
| Vaseline (Vaseline Codex A from Synteal) | | 5 | 5 | 5 |
| Sodium carboxymethyl cellulose (CMC Blanose 7H4XF from Aschland) | 14.8 | 14.8 | 15 | 15 |
| Metformin from Fukang | 5 | 5 | 5 | 5 |
| copolymer of the salt of 2-methyl-2[(1-oxo-2-propenyl)amino]-1-propanesulfonic acid and of 2-hydroxyethyl ester of propenoic acid (Sepinov EMT 10 from SEPPIC) | 2 | 2 | 2 | 2 |

[1]As the viscosities of the two Kraton are different, Kraton G1651 E was introduced in order to obtain a similar viscosity for the formulations of examples 15 and 16.

TABLE 18

| | Average cumulative release (μg/cm²) | | | | | |
|---|---|---|---|---|---|---|
| Example | 0 h | 4 h | 7 h | 24 h | 48 h | 72 h |
| Example 13 | 0 | 481 | 563 | 647 | 711 | 748 |
| Example 14 | 0 | 472 | 560 | 645 | 717 | 756 |
| Example 15 | 0 | 357 | 420 | 509 | 594 | 641 |
| Example 16 | 0 | 343 | 398 | 495 | 597 | 666 |

TABLE 19

| | Average non-cumulative release (μg/cm²) | | | | | |
|---|---|---|---|---|---|---|
| Example | 0 h | 4 h | 7 h | 24 h | 48 h | 72 h |
| Example 13 | 0 | 481 | 82 | 84 | 64 | 37 |
| Example 14 | 0 | 472 | 88 | 84 | 72 | 39 |
| Example 15 | 0 | 357 | 63 | 89 | 85 | 48 |
| Example 16 | 0 | 343 | 55 | 97 | 102 | 69 |

Figure 6:
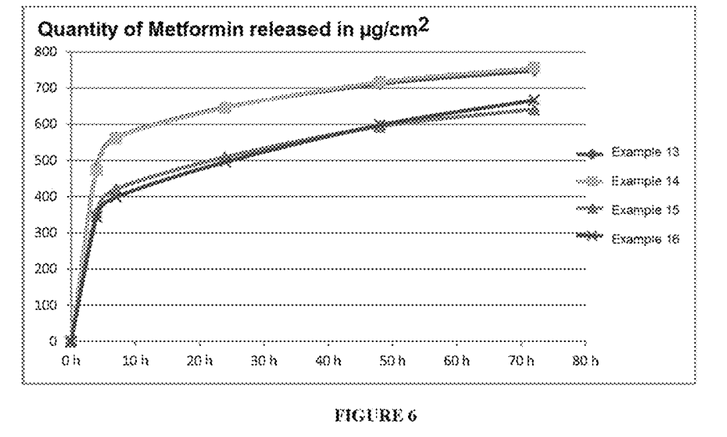
FIG. 6 is a graphical representation of the cumulative dissolution profiles, evaluated in µg/cm$^2$ of active principle released from dressings described from the example 13 to the example 16.

FIG. 6 is a graphical representation of the cumulative release of examples 13 to 16.

Figure 7:
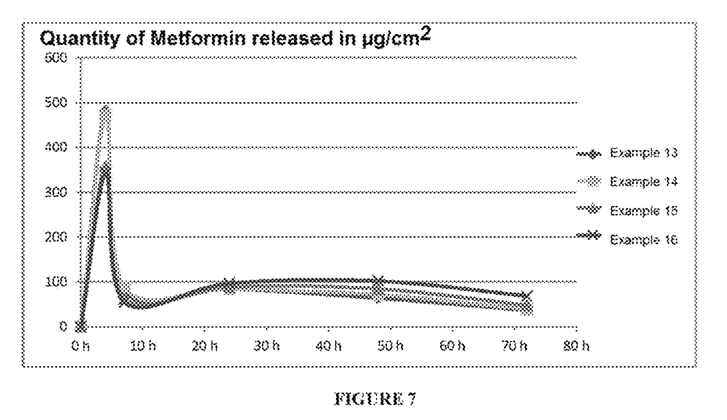
FIG. 7 is a graphical representation of the non-cumulative dissolution profiles, evaluated in µg/cm$^2$ of active principle released from dressings described from the example 13 to the example 16.

FIG. 7 is a graphical representation of the non-cumulative release of examples 13 to 16.

The models of examples 13 to 16 tested have a similar release profile. However, the release values obtained make it possible to distinguish the models of examples 13 and 14 from the models of examples 15 and 16. Indeed, at 72 h, the models of examples 13 and 14 release approximately 86% of metformin. The presence or not of vaseline therefore has no impact on the release. The models of examples 15 and 16, however release approximately 75% of metformin at 72 h without revealing any impact in the change of oil (Puretol vs. Pionier) on the released quantities of metformin.

The difference between the models resides in the grade of Kraton used (G1654® for the models of examples 13 and 14 vs. G1651® for the models of examples 15 and 16).

The results obtained show a more progressive release (better release profile) by using Kraton G1651®.

Examples 17 to 20

TABLE 20

| Commercial ref. | Ex. 17 % by weight | Ex. 18 % by weight | Ex. 19 % by weight | Ex. 20 % by weight |
|---|---|---|---|---|
| SEBS (Kraton G1654 ES from Kraton Polymer) | 6 | 6 | 6.34 | 6.34 |
| White mineral oil (Ondina 919 from Shell) | 72.88 | 72.88 | | |
| White naphthenic oil (Pionier 2076P from Hansen&Rosenthal) | | | 71.74 | 71.74 |
| Pentacrythitol Tetrakis3-(3,5-di-tert-butyl-4-hydroxyphenyl)propionate (Irganox 1010 from BASF) | 0.12 | 0.12 | 0.12 | 0.12 |
| Sodium carboxymethyl cellulose (CMC Blanose 7H4XF from Aschland) | 14 | 14 | 14.8 | 14.8 |
| copolymer of the salt of 2-methyl-2[(1-oxo-2-propenyl)amino]-1-propanesulfonic acid and of 2-hydroxyethyl ester of propenoic acid (Sepinov EMT 10 from SEPPIC) | 2 | 2 | 2 | 2 |
| Metformin from Fukang | 5 | | | |
| Metformin from Wanbury | | 5 | | |
| Metformin from Weifa | | | 5 | |
| Metformin from IPCA | | | | 5 |

The metformins tested in the examples 17 to 20 are distinguished by their particle size as explained in the following table:

| Example | Population | d50 (µm) | d90 (µm) |
|---|---|---|---|
| Example 17 (Metformin from Fukang) | Unimodal | 125 | 264 |
| Example 18 | Bimodal | 443 | 1123 |
| Example 19 | Unimodal | 75 | 195 |
| Example 20 | Unimodal | 182 | 509 |

TABLE 21

| | Average cumulative release (µg/cm²) | | | | | |
|---|---|---|---|---|---|---|
| Example | 0 h | 4 h | 7 h | 24 h | 48 h | 72 h |
| Example 17 | 0.00 | 504.59 | 586.15 | 650.49 | 688.83 | 708.24 |
| Example 18 | 0.00 | 370.59 | 442.28 | 504.08 | 535.39 | 553.83 |
| Example 19 | 0.00 | 315.27 | 379.15 | 455.69 | 503.16 | 532.00 |
| Example 20 | 0.00 | 500.08 | 587.71 | 662.05 | 706.56 | 730.12 |

TABLE 22

| | Average non-cumulative release (µg/cm2) | | | | | |
|---|---|---|---|---|---|---|
| Example | 0 h | 4 h | 7 h | 24 h | 48 h | 72 h |
| Example 17 | 0.00 | 504.59 | 81.56 | 64.34 | 38.34 | 19.41 |
| Example 18 | 0.00 | 370.59 | 71.69 | 61.80 | 31.31 | 18.44 |

TABLE 22-continued

| | Average non-cumulative release (µg/cm2) | | | | | |
|---|---|---|---|---|---|---|
| Example | 0 h | 4 h | 7 h | 24 h | 48 h | 72 h |
| Example 19 | 0.00 | 315.27 | 63.88 | 76.54 | 47.47 | 28.84 |
| Example 20 | 0.00 | 500.08 | 87.63 | 74.34 | 44.51 | 23.56 |

Figure 8:
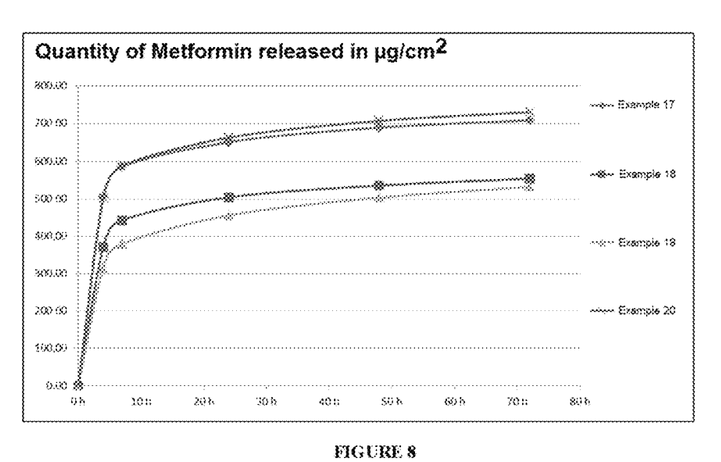
FIG. 8 is a graphical representation of the cumulative dissolution profiles, evaluated in µg/cm$^2$ of active principle released from dressings described from the example 17 to the example 20.

FIG. 8 is a graphical representation of the cumulative release of examples 17 to 20.

Figure 9:
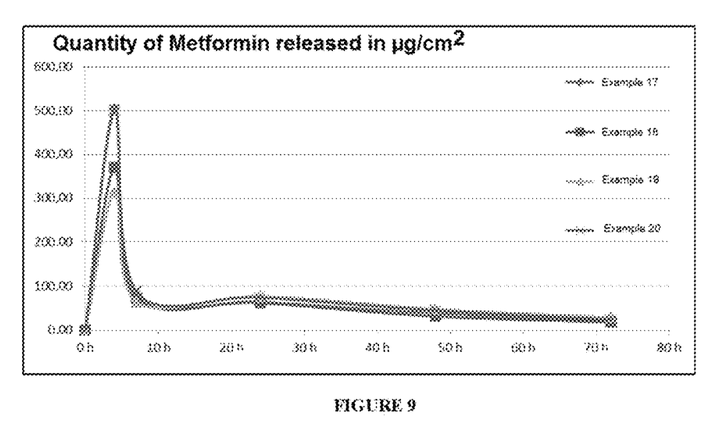
FIG. 9 is a graphical representation of the non-cumulative dissolution profiles, evaluated in µg/cm$^2$ of active principle released from dressings described from the example 17 to the example 20.
Figure 10:
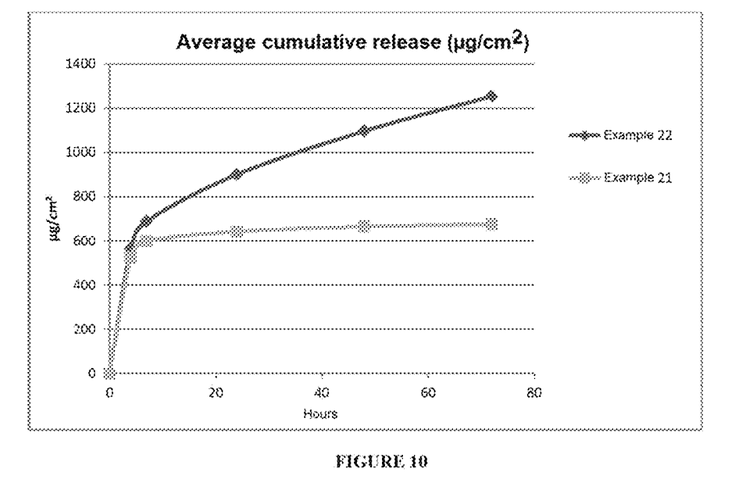
FIG. 10 is a graphical representation of the cumulative dissolution profiles, evaluated in µg/cm$^2$ of released active principle from dressings described in the examples 21 and 22.
Figure 11:
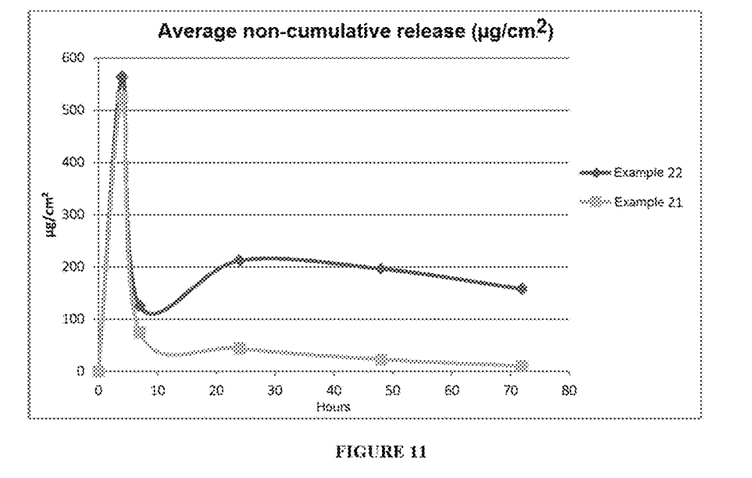
FIG. 11 is a graphical representation of the non-cumulative dissolution profiles, evaluated in µg/cm$^2$ of released active principle from dressings described in the examples 21 and 22.

FIG. 9 is a graphical representation of the non-cumulative release of examples 17 to 20.

Examples 21 and 22

TABLE 23

| Commercial ref. | Ex. 21 % by weight | Ex. 22 % by weight |
|---|---|---|
| SEBS (Kraton G1654 ES from Kraton Polymer) | 5.7 | 5.7 |
| SEBS (Kraton G1650 E from Kraton Polymer) | 2.6 | 2.6 |
| White mineral oil (Ondina 919 from Shell) | 57 | 57 |
| Pentacrythitol Tetrakis3-(3,5-di-tert-butyl-4-hydroxyphenyl)propionate (Irganox 1010 from BASF) | 0.2 | 0.2 |
| Sodium carboxymethyl cellulose (CMC Blanose 7H4XF from Aschland) | 14 | 14 |
| Vaseline-mixture of paraffin, liquid paraffin and wax (Vaseline Codex A from Synteal) | 13.5 | 13.5 |
| copolymer of the salt of 2-methyl-2[(1-oxo-2-propenyl)amino]-1-propanesulfonic acid and of 2-hydroxyethyl ester of propenoic acid (Sepinov EMT 10 from SEPPIC) | 2 | 2 |
| Metformin from Fukang | 5 | 5 |

TABLE 24

| | Average cumulative release (μg/cm²) | | | | | |
|---|---|---|---|---|---|---|
| Example | 0 h | 4 h | 7 h | 24 h | 48 h | 72 h |
| Example 21 | 0.00 | 524.28 | 598.51 | 642.15 | 664.97 | 675.08 |
| Example 22 | 0.00 | 563.24 | 688.07 | 900.24 | 1096.63 | 1254.29 |

TABLE 25

| | Average non-cumulative release (μg/cm²) | | | | | |
|---|---|---|---|---|---|---|
| Example | 0 h | 4 h | 7 h | 24 h | 48 h | 72 h |
| Example 21 | 0.00 | 524.28 | 74.23 | 43.64 | 22.83 | 10.11 |
| Example 22 | 0.00 | 563.24 | 124.83 | 212.17 | 196.39 | 157.67 |

The most interesting releases were obtained with the examples 17, 19, 20 and 22. Indeed, the cumulative release curve (FIG. 8) shows that, although releasing a sufficient quantity of metformin, the example 18 has a progression in the release of metformin that is not as high as that of the other examples. The non-cumulative release curve shows that after 10 h, the curve of the example 18 is that which releases the least amount of metformin.

The example 22 revealed an unexpected release: indeed, when the elastomeric matrix is used in a self-supporting interface dressing, the release of metformin is improved with respect to the same matrix coated on one weave.

Furthermore, surprisingly and unexpectedly, the samples of metformin having a particle size of small dimension are those for which the dissolution was the slowest. Yet, usually, the smaller the particle size is, the faster the dissolution is.

The best results were obtained with a metformin of which the particle size has a unimodal distribution. Preferably the particle size is d50<200 μm, d90<510 μm.

The invention claimed is:

1. A dressing comprising an interface layer comprising an elastomeric matrix, said matrix comprising metformin, the salts and the complexes thereof, wherein the metformin has a particle size defined by 75 μm<d50<300 μm and 195 μm<d90<600 μm.

2. The dressing according to claim 1, wherein the elastomeric matrix comprises an elastomer chosen from triblock sequenced polymers of the ABA type comprising two terminal A styrene blocks and a central sequence B which is a saturated olefin such as for example ethylene-butylene or ethylene-propylene.

3. The dressing according to claim 1, wherein the elastomeric matrix comprises at least one elastomer, said elastomer being a poly(styrene-(-ethylene-butylene-)-styrene) triblock sequenced polymer.

4. The dressing according to claim 1, wherein the metformin has a particle size defined by 75 μm<d50<200 μm and 75 μm<d90<510 μm.

5. The dressing according to claim 1, wherein the elastomeric matrix comprises a plasticiser and/or a hydrocolloid.

6. The dressing according to claim 1, wherein the plasticiser is a mixture of mineral oil.

7. The dressing according to claim 1, wherein the elastomeric matrix comprises at least one releasing agent chosen from the copolymer of the salt of 2-methyl-2[(1-oxo-2-propenyl)amino]-1-propanesulfonic acid and of 2-hydroxyethyl ester of propenoic acid or of the mixture of 2-octyl-1-dodecanol, D-xylopyranoside, 2-octyldodecyl and polyethyleneglycol 30 dipolyhydroxystearate.

8. The dressing according to claim 1, wherein the elastomeric matrix consists substantially:
   0.5 to 15%, in relation to the total weight of the matrix, of metformin having a particle size defined by 75 μm<d50<300 μm and 195 μm<d90<600 μm, the salts or the complexes thereof;
   2 to 15%, in relation to the total weight of the matrix, of at least one elastomeric polymer;
   1 to 25%, in relation to the total weight of the matrix, of at least one hydrocolloid;
   45 to 95%, in relation to the total weight of the matrix, of at least one plasticiser;
   0.05 to 1%, in relation to the total weight of the matrix, of at least one agent antioxidant;
   0.01 to 10%, in relation to the total weight of the matrix, of a releasing agent chosen from the copolymer of the salt of 2-methyl-2[(1-oxo-2-propenyl)amino]-1-propanesulfonic acid and of 2-hydroxyethyl ester of propenoic acid or the mixture of 2-octyl-1-dodecanol, D-xylopyranoside, 2-octyldodecyl and polyethyleneglycol 30 dipolyhydroxystearate.

9. The dressing according to claim 1, wherein the elastomeric matrix consists substantially:
   0.5 to 15%, in relation to the total weight of the matrix, of metformin having a particle size defined by 75 μm<d50<300 μm and 195 μm<d90<600 μm, the salts or the complexes thereof;
   2 to 15%, in relation to the total weight of the matrix, of at least one elastomeric polymer;
   1 to 25%, in relation to the total weight of the matrix, of at least one hydrocolloid compound;
   45 to 95%, in relation to the total weight of the matrix, of at least one plasticiser;
   0.01 to 10%, in relation to the total weight of the matrix, of a releasing agent chosen from the copolymer of the salt of 2-methyl-2[(1-oxo-2-propenyl)amino]-1-propanesulfonic acid and of 2-hydroxyethyl ester of propenoic acid or the mixture of 2-octyl-1-dodecanol, D-xylopyranoside, 2-octyldodecyl and polyethyleneglycol 30 dipolyhydroxystearate.

10. The dressing according to claim 1, wherein the percentage of metformin released after 72 hours is between 40 and 100% of the quantity of metformin inserted in the dressing.

11. A method of producing the dressing according to claim 1 comprising:
   i. preparing an interface layer formed from an elastomeric matrix by:
      a. preparing an elastomeric matrix by dispersion of the metformin having a particle size defined by 75 μm<d50<300 μm and 195 μm<d90<600 μm, the salts and the complexes thereof in an elastomer,
      b. coating of a weave with the elastomeric matrix prepared in the step i or the hot casting of said matrix,
   ii. optionally the covering of the interface layer with at least one absorbent layer
   iii. optionally the maintaining of the interface layer and of the possible absorbent layer by a strip or an adhesive support intended to be fastened onto the peripheral zones of healthy skin far from the wound.

12. A method of healing a wound in a subject having a wound comprising contacting the wound with the dressing of claim 1.

* * * * *